(12) United States Patent
Dieker et al.

(10) Patent No.: US 11,608,445 B2
(45) Date of Patent: Mar. 21, 2023

(54) OLIGOMERIC AMINOKETONES AND THEIR USE AS PHOTOINITIATORS

(71) Applicant: SUN CHEMICAL CORPORATION, Parsippany, NJ (US)

(72) Inventors: Jürgen Dieker, Karlstein am Main (DE); Kai-Uwe W. Gaudl, Karlstein am Main (DE)

(73) Assignee: Sun Chemical Corporation, Parsippany, NJ (US)

( * ) Notice: Subject to any disclaimer, the term of this patent is extended or adjusted under 35 U.S.C. 154(b) by 0 days.

(21) Appl. No.: 17/494,038

(22) Filed: Oct. 5, 2021

(65) Prior Publication Data

US 2022/0112384 A1 Apr. 14, 2022

Related U.S. Application Data

(60) Provisional application No. 63/091,343, filed on Oct. 14, 2020.

(51) Int. Cl.
| | | |
|---|---|---|
| *C09D 11/10* | (2014.01) | |
| *C07C 229/52* | (2006.01) | |
| *C09D 11/101* | (2014.01) | |
| *C09D 11/107* | (2014.01) | |
| *C09D 133/04* | (2006.01) | |
| *C09D 4/00* | (2006.01) | |

(52) U.S. Cl.
CPC .......... *C09D 11/101* (2013.01); *C07C 229/52* (2013.01); *C09D 4/00* (2013.01); *C09D 11/107* (2013.01); *C09D 133/04* (2013.01)

(58) Field of Classification Search
CPC .. C09D 11/101; C09D 11/107; C09D 133/04; C09D 4/00; C09C 299/52
See application file for complete search history.

(56) References Cited

U.S. PATENT DOCUMENTS 10,563,073 B2 2/2020 Gaudl

*Primary Examiner* — Sanza L. McClendon
(74) *Attorney, Agent, or Firm* — Marian E. Fundytus; Ostrolenk Faber LLP

(57) ABSTRACT

The invention relates to photoactive oligomeric aminoketones for compositions and inks curable with ultraviolet (UV) light. The oligomeric ketones are particularly useful for printing or coating materials wherein a low migration of photoinitiators, and reduced transfer of ink from the printed to another surface are desired, such as, for example, food packaging.

9 Claims, 1 Drawing Sheet

UV-Absorption Spectrum of Inventive Example I (in THF)

UV-Absorption Spectrum of Inventive Example I (in THF)
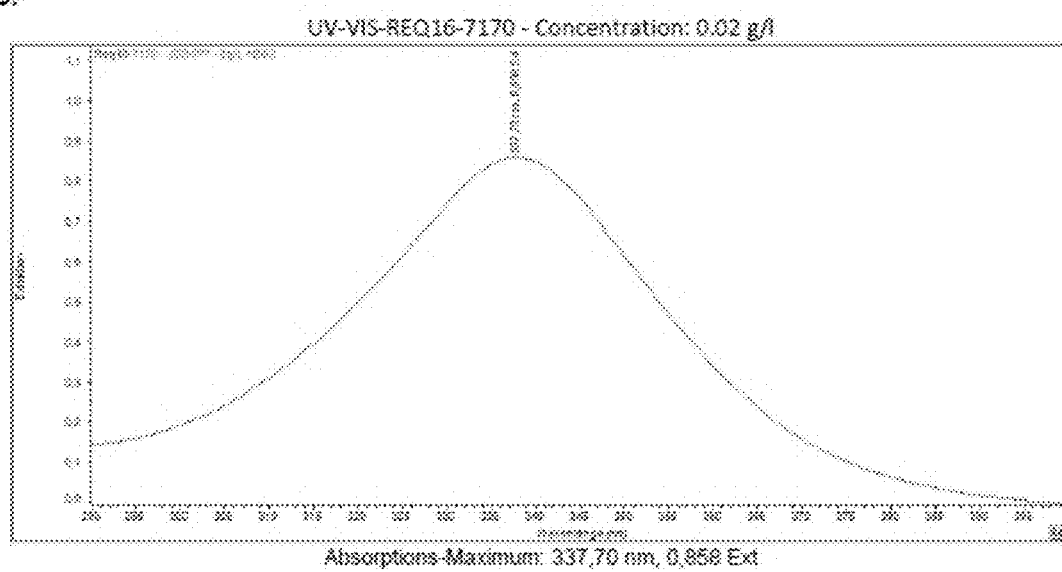

OLIGOMERIC AMINOKETONES AND THEIR USE AS PHOTOINITIATORS

This application claims priority to U.S. Provisional Patent Application Ser. No. 63/091,343, filed Oct. 14, 2020, which is hereby incorporated herein in its entirety.

FIELD OF THE INVENTION

The present invention relates to oligomeric aminoketones that are useful as photoinitiators in UV-curable coatings and inks. The oligomeric aminoketones of the invention are particularly useful for coatings and inks to use for printing or coating materials wherein a low migration of photoinitiators is required, such as food packaging.

BACKGROUND

Radiation curable compositions containing acrylic acid ester groups can be cured by exposure to ultraviolet light (UV). For a fast curing composition, a photoinitiator is necessary, which forms radicals under irradiation with photons and initiates free-radical polymerization of the acrylate groups, which then leads to a hardening (curing) of the product.

However, radiation curable compositions containing photoinitiators can be a challenge for several applications in packaging, especially in food packaging ("Radiation curing in packaging", Radtech Report March/April 2006). Residual photoinitiators, as well as their cleavage products, remain in the coating or ink and may cause problems, such as for example migration, contamination, odor or off taste. For example, residues of photoinitiators and cleavage products can migrate through the substrate and affect adjacent products such as food stuff or may contaminate food by offset contact migration. Therefore, there is a continuous search for photoinitiator systems which have low potential for migration and odor.

As described in the literature (L. L. Katan in "Migration of additive food contact", Black Academical & Professional, first edition, London 1996, page 97, table 5.3), the ability of a material to migrate is governed by its molecular weight, rather than by its chemical structure. Therefore, for a low migration UV-curable ink or coating, photoactive components having a molecular weight of >500-1,000 Daltons are preferred.

Oligomeric and polymeric tertiary aromatic amines are used in the art to enhance the UV-curing response of radiation curable compositions ("Industrial Photoinitiators", CRC press London 2010, page 106). Together with ketones, they can form type-II photoinitiators. Tertiary amines are especially useful for the surface cure of UV-inks and UV-coatings as they are able to transform non-reactive oxoradicals, which are deactivated by reaction with oxygen, into more reactive radicals and reduce the inhibiting effect of oxygen on the polymerization on the surface of inks and coatings, ("Photoinitiators for free radical and cationic & anionic photo-polymerization", Wiley & Sons 1998, page 84).

Moreover, unlike type-I photoinitiators, type-II photoinitiators usually do not form small molecules (splitting products) and are therefore especially useful in applications requiring low migration of chemical species.

Among the most reactive amines proposed for low migration applications are oligomeric aminobenzoates. Examples of oligomeric aminobenzoates for low migration applications are, for example, Genopol AB-1 and AB-2 (products of Rahn Group, Switzerland) and Omnipol ASA (product of IGM Resins, Netherlands). However, aminobenzoates still need a partner to form an effective initiator system, such as an aromatic ketone or thioxanthone.

In contrast, aromatic aminoketones, besides the tertiary amino group, already contain an aromatic ketone, which can be excited by UV-light and additionally contribute to UV-cure. An example of an oligomeric aminoketone for low migration applications is Omnipol SZ (IGM Resins).

U.S. Pat. No. 10,563,073 discloses oligomeric aminoketones suitable as photoinitiators in applications that require low migration of photoinitiators. The oligomeric aminoketones of this patent are not substituted on the aromatic ring bearing the nitrogen substituent.

Moreover, due to recent developments of UV-bulbs emitting predominantly in the UV-A area, and which do not produce ozone and exhibit a low energy consumption, there is a constant search for photoactive materials especially useful for UV-A curing to make the UV-technology safer in relation to both migration and process safety.

SUMMARY OF THE INVENTION

The present invention provides novel oligomeric aminoketones according to general formula I, shown below. In certain embodiments, the oligomeric aminoketones are useful as photoinitiators in UV-curable compositions. In other embodiments, the UV-curable compositions are UV-curable coatings or inks. The oligomeric aminoketones are particularly useful for printing or coating materials wherein a low migration of chemical species is required.

The present invention provides novel aminoketones of the general Formula I:

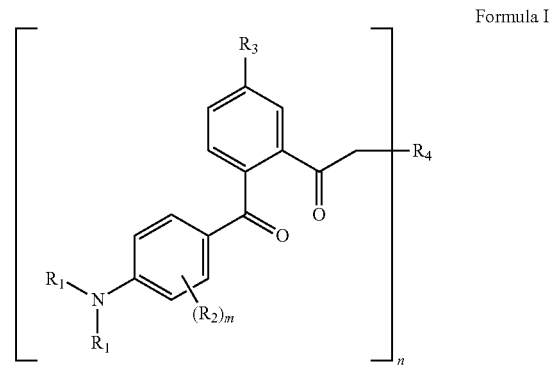

Formula I wherein
Each $R^1$ is independently selected from branched or unbranched $C_{1-12}$ alkyl, or $C_{3-12}$ cycloalkyl radical; each of which is independently optionally substituted with $R^5$;
$R^4$ is selected from the group consisting of a di-, tri-, tetra-, penta- and hexavalent alkyl radical, wherein $CH_2$ groups may optionally be replaced by an oxygen or substituted by hydroxyl-functions as a result of the reaction with glycidyl or epoxy-compounds;
$R^3$ is selected from the group consisting of H, a branched or unbranched $C_{1-12}$ alkyl, and a $C_{3-12}$ aryl radical;
each $R^5$ is independently selected from the group consisting of oxygen, nitrogen, and sulfur;
each $R^2$ is independently selected from branched or unbranched $C_{1-12}$ alkyl, or $C_{3-12}$ cycloalkyl, preferably $C_1$ to $C_4$ alkyl. $R^2$ can substitute one (m=1), two (m=2), three (m=3), or all four (m=4) hydrogens on the aromatic ring bearing the amino-substituent; and when $R^4$ is formed by the reaction with a glycidyl ether or epoxy-compounds then n denotes an integer from 1 to 4; in all other instances, n denotes an integer from 2 to 6.

In one embodiment, the present invention provides novel compositions comprising one or more aminoketones of Formula I, and one or more acrylates.

In one embodiment, the present invention provides novel UV-curable coatings or inks comprising one or more aminoketones of Formula I, and one or more acrylates.

In another embodiment, the UV-curable coatings or inks are curable with UV light having a wavelength of 310-400 nm.

In certain embodiments, the UV-curable coatings or inks further comprise a colorant.

In certain embodiments, the UV-curable coatings or inks comprising an aminoketone according to Formula I are capable of being cured by a light emitting diode (LED).

In another embodiment, the UV-curable coatings or inks comprising an aminoketone according to Formula I comprise no splitting type photoinitiators.

In a certain embodiment, the present invention provides low migration printed material comprising a UV-curable coating or ink according to any one of Formula I.

In another embodiment, the cured material is obtained by curing with UV radiation curing of the UV-curable coatings or inks described above.

BRIEF DESCRIPTION OF THE DRAWING

The FIGURE shows the UV absorption spectrum of the aminoketone composition of Inventive Example I.

DETAILED DESCRIPTION OF THE INVENTION

The present invention relates to photoactive oligomeric aminoketones for compositions curable with ultraviolet (UV) light. More specifically, the photoactive oligomeric aminoketones are suitable for radiation curable low migration printing inks and coatings.

It is an object of the present invention to provide effective oligomeric aminoketones which are useful in photoinitiator systems, especially for low migration coatings and inks. Another object of the present invention is to provide a low migration coating and ink free of any thioxanthone based photoinitiator.

The present invention provides novel aminoketones of the general Formula I:

Formula I wherein

Each $R^1$ is independently selected from branched or unbranched $C_{1-12}$ alkyl, or $C_{3-12}$ cycloalkyl radical; each of which is independently optionally substituted with $R^5$;

$R^4$ is selected from the group consisting of a di-, tri-, tetra-, penta- and hexavalent alkyl radical, wherein CH2 groups may optionally be replaced by an oxygen or substituted by hydroxyl-functions as a result of the reaction with glycidyl or epoxy-compounds;

$R^3$ is selected from the group consisting of H, a branched or unbranched $C_{1-12}$ alkyl, and a $C_{3-12}$ aryl radical;

each $R^5$ is independently selected from the group consisting of oxygen, nitrogen, and sulfur;

each $R^2$ is independently selected from branched or unbranched $C_{1-12}$ alkyl, or $C_{3-12}$ cycloalkyl, preferably $C_1$ to $C_4$ alkyl. $R^2$ can substitute one (m=1), two (m=2), three (m=3), or all four (m=4) hydrogens on the aromatic ring bearing the amino-substituent; and when $R^4$ is formed by the reaction with a glycidyl ether or epoxy-compounds then n denotes an integer from 1 to 4; in all other instances, n denotes an integer from 2 to 6.

The aminoketones of general Formula I preferably show an ultraviolet absorption maxima of 325 nm to 365 nm, and a high reactivity in radiation curable coatings and inks. The aminoketones of Formula I are further preferably curable by UV-A radiation.

In the last few years, due to the development of doped UV light bulbs emitting at longer wavelengths in the UV-A area, at 310-400 nm, and the development of high powered light emitting diodes (LED) emitting at 365-395 nm, it has become more and more attractive to commercially use such light sources because there is no ozone formation, and lower energy consumption, so that this technology is regarded as a "greener" solution.

However, there is a limited source of oligomeric photoreactive materials having light absorption in the UV-A area, especially in the region of 365-395 nm of light emitting diodes (LED).

Therefore, the invention also provides oligomeric aminoketones of the general Formula I, having longer wavelength absorption maxima >330 nm, and overlapping with the emission of LED bulbs.

The oligomeric aminoketones of the general Formula I can be made, for example, by a Friedel-Crafts acylation of aromatic amines with phthalic anhydride or acid chlorides followed by esterification with a multifunctional alcohol.

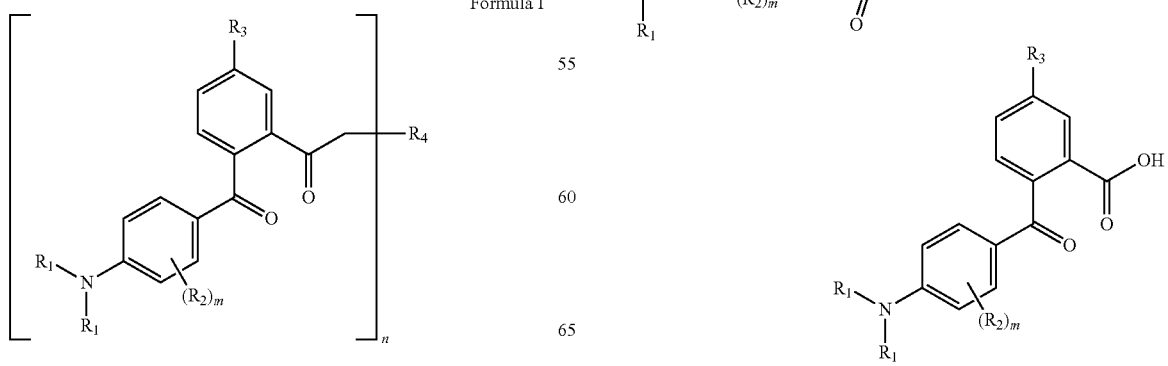

-continued
Precursor for Formula I

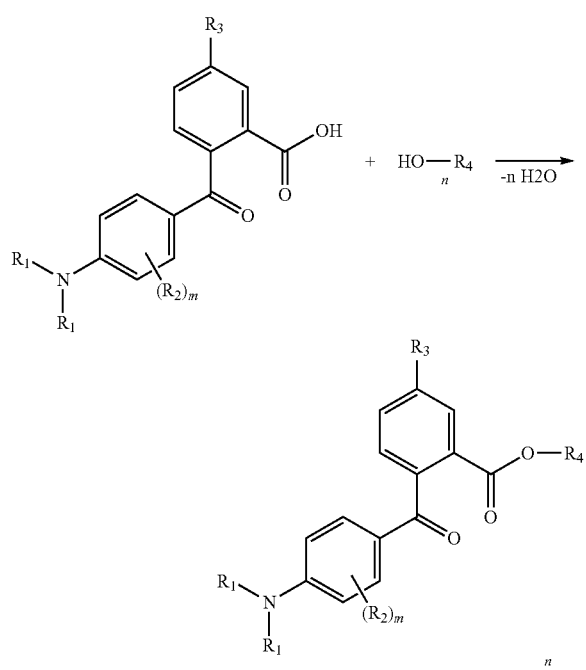

or alternatively from epoxides/glycidylethers:

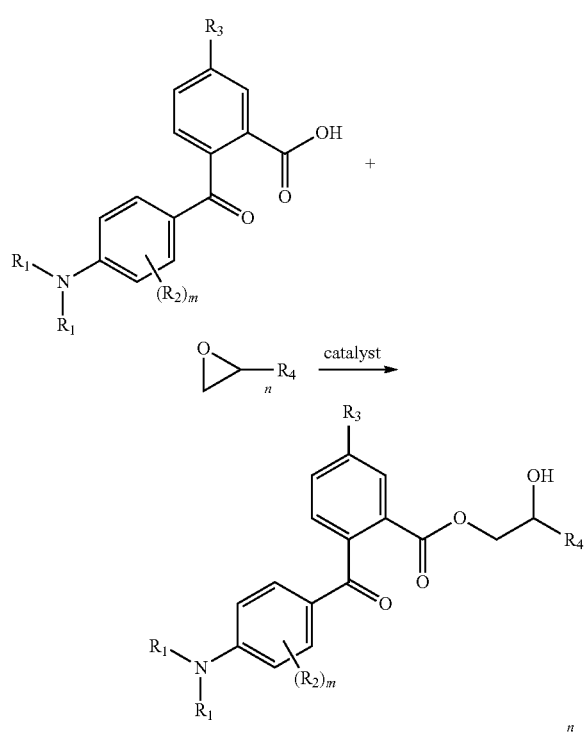

and isomers where the chromophor is attached to the secondary OH-functionality.

wherein the $R^4$ in Formula I would mean $R^4$—CH(OH)—CH$_2$—] in the case of epoxides, or $R^4$—O—CH$_2$—CH(OH)—CH$_2$—O—] and the isomers in the case of glycidyl ethers.

General methods of acylation are described in the literature (Organikum, Wiley-VHC, $22^{nd}$ edition, page 380). Usually, amine and anhydride, and an optional solvent, are dissolved in each other and aluminum trichloride is added, so that the temperature does not exceed 30° C. Then, the reaction is allowed to complete, and the mixture is poured into acidified water. Then, the precipitated solid is collected, filtered, washed, and dried. The intermediate acids are colorless to slightly pale yellow to faint greenish solids, which are soluble in the common solvents, as well as alkaline water. This also offers the possibility to purify the intermediate acids by dissolving in alkaline water and precipitation by acidification with an acid such as diluted sulfuric acid.

Though the Friedel-Crafts reaction is similar to the one described in our earlier patent U.S. Ser. No. 10/563,073B2, the additional group R2 on the aromatic ring which is also bearing the amino-group is an advantage over the reaction described in U.S. Ser. No. 10/563,073B2, because it leads to a more defined product blocking the ortho-position. This results in a more defined and purer intermediate which is desired especially for low-migration/food-packaging applications. Furthermore, some of the toluidine derivatives and, even more importantly, some of the resulting products of the reaction shown in above are already known, commercially available and therefore registered, which means that these substances were already evaluated and studied for their toxicological effects which is an advantage over the products of the aniline-derivatives described in U.S. Ser. No. 10/563,073B2 where little or nothing is known about the toxicological effects. Also the poly(propylene glycol) diglycidyl ether is a registered and evaluated substance (e.g. it is on the Swiss list) which means the polymer formed by the reaction described above results in a more defined product (not a product mixture if e.g. the ortho-position is blocked) and starts from starting materials which better comply with regulatory/toxicity constraints, because the starting materials were already tested and Reach pre-registered and may even be commercially available (e.g. methyl,N,N-diethyl-amino-benzoylbenzoic acid (CAS: 52830-65-6).

Then, in a final step, the acids are esterified with alcohols, preferably with di-, tri-, tetra, penta- and hexavalent polyols such as ethylene glycol, 1,4-butandiol, 1,6-hexandiol, dipropylene glycol, neopentylglycol, ethoxylated neopentylglycol, propoxylated neopentylglycol, tripropylene glycol, ethoxylated bisphenol-A, poly(ethylene)glycol, trimethylolpropane, ethoxylated trimethylolpropane, propoxylated trimethylolpropane, propoxylated glycerol, pentaerythritol, ethoxylated pentaerythritol, propoxylated pentaerythritol, alkoxylated pentaerythritol, ditrimethylolpropane, dipentaerythritol, dipentaerythritol or mixtures thereof, preferred are ethoxylated trimethylolpropanes, ethoxylated pentaerythritols and propoxylated pentaerythritol, and the like.

Usually an acid catalyst, such as methane sulfonic acid or sulfuric acid, or a metal catalyst, such as titanium tetrabutylate or butyl tin hydroxyoxide, is suitable. The formed water can be removed physically by the help of an entrainer such as toluene, a nitrogen gas stream, vacuum, or chemically by the reaction with a water up-taking chemical, such as a carbodiimide.

Alternatively, the esterification can also be done with a multifunctional epoxide, such as bisphenol A-diglycidyl ether or Poly-ethylene glycol diglycidylether or poly-propylene glycol diglycidylether both with molecular weights between 250 Da and 2500 Da, under catalysis with triphenylphosphine or an ammonium salt, such as tetraethylammonium bromide. The products are viscous to highly viscous, pasty to solid yellow to brownish materials, having a molecular weight of 500 to 2,000 Daltons, an absorption maximum of 330-375 nm, and a molar extinction coefficient of 10,000-55,000 liter·mol$^{-1}$·cm$^{-1}$.

The FIGURE shows the absorption spectra of a compound of the general Formula I. It is clear that the aminoketone is able to catch light from a doped mercury bulb having strong emission in UV-A light area of 310-400 nm. Compositions comprising the aminoketone will therefore have improved through cure and surface cure properties.

A photoinitiator blend containing the inventive structure of formula I (Example 3) was prepared and was investigated in comparison to a Standard PI blend (Example 2) which uses a Thioxanthone instead in a magenta Sun Chemical Laser ink. The blend was made by mixing the PI compounds in ratios described in Table 1.

Genopol AB-2 is a multifunctional aminobenzoate derivative designed for use in UV-curable inks, coatings and adhesives, where low migration and low odor is desired. Commercially available from RAHN company, Switzerland.

Oligomeric synergist Omnipol TX is a difunctional thioxanthone photoinitiator specifically designed for use in inks requiring low migration and low volatility. It is particularly suited to use in offset printing inks as an alternative to Omnirad ITX (Isopropyl thioxanthone) in combination with other photoinitiators and amine synergists, all commercially available from IGM Resins.

Omnipol BP is a difunctional benzophenone photoinitiator specifically designed for use in inks and coatings requiring low migration and low volatility. Commercially available from IGM Resins.

The aminoketones of the general Formulae I are useful in radiation curable compositions which can be UV-cured by an actinic light source, such as UV-light, provided by a high-voltage mercury bulb, a medium-voltage mercury bulb, a xenon bulb, a carbon arc lamp, a metal halide bulb, an UV-LED lamp, or sunlight. The wavelength of the applied irradiation is within a range of 310 to 500 nm, preferably 320 to 395 nm.

Due to the high molar extinction coefficients of the aminoketones of the general Formula I, they are especially suitable for radiation curable printing inks, such as, for example, a UV-flexographic ink, a UV-jet ink, a UV-gravure ink or a UV-offset ink. The high extinction coefficient also allows UV-curing in highly pigmented systems, in which pigments and photoinitiators are competitors for the available UV radiation. The inks are made according to the methods known in the art, such as, for example, dispersing a pigment in the radiation curable compositions of this invention with a bead mill or a three roll mill until the desired particle size and color strength is achieved.

The energy curable inks may contain one or more colorants in the form of a dye or pigment dispersed therein. Pigments suitable for use in the present invention include conventional organic or inorganic pigments. Representative pigments may, for example, be selected from the group of Pigment Yellow 1, Pigment Yellow 3, Pigment Yellow 12, Pigment Yellow 13, Pigment Yellow 14, Pigment Yellow 17, Pigment Yellow 63, Pigment Yellow 65, Pigment Yellow 73, Pigment Yellow 74, Pigment Yellow 75, Pigment Yellow 83, Pigment Yellow 97, Pigment Yellow 98, Pigment Yellow 106, Pigment Yellow 111, Pigment Yellow 114, Pigment Yellow 121, Pigment Yellow 126, Pigment Yellow 127, Pigment Yellow 136, Pigment Yellow 138, Pigment Yellow 139, Pigment Yellow 174, Pigment Yellow 176, Pigment Yellow 188, Pigment Yellow 194, Pigment Orange 5, Pigment Orange 13, Pigment Orange 16, Pigment Orange 34, Pigment Orange 36, Pigment Orange 61, Pigment Orange 62, Pigment Orange 64, Pigment Red 2, Pigment Red 9, Pigment Red 14, Pigment Red 17, Pigment Red 22, Pigment Red 23, Pigment Red 37, Pigment Red 38, Pigment Red 41, Pigment Red 42, Pigment Red 48: 2, Pigment Red 53: 1, Pigment Red 57: 1, Pigment Red 81: 1, Pigment Red 112, Pigment Red 122, Pigment Red 170, Pigment Red 184, Pigment Red 210, Pigment Red 238, Pigment Red 266, Pigment Blue 15, Pigment Blue 15: 1, Pigment Blue 15: 2, Pigment Blue 15: 3, Pigment Blue 15: 4, Pigment Blue 61, Pigment Green 7, Pigment Green 36, Pigment Violet 1, Pigment Violet 19, Pigment Violet 23, Pigment Black 7, and the like.

The radiation curable compositions and inks of this invention may contain the usual additives to modify flow, surface tension, gloss and abrasion resistance of the cured coating or printed ink.

Such additives contained in inks or coatings typically are a surface-active agent, a wax, or a combination thereof. These additives may function as leveling agents, wetting agents, slip agents, dispersants and de-aerators. Preferred additives include fluorocarbon surfactants, silicones, organic polymer surfactants, and inorganic materials such as talc. Examples include the Tegorad™ product lines (commercially available from Tego Chemie, Essen, Germany) and the Solsperse™ product lines (commercially available products from Lubrizol Company).

The radiation curable compositions of the present invention may optionally contain small amounts of additional type-I and type-II photoinitiators such as, for example, benzophenones, benzylketals, dialkoxy acetophenones, hydroxyalkylacetophenones, aminoalkylphenones, acylphosphinoxides and thioxanthones, for example benzophenone, methylbenzophenone, 4-phenylbenzophenone, 4,4'-bis(dimethylamino)-benzophenone, 4,4'-bis(diethylamino)-benzophenone, 2,2-dimethoxy-2-phenylacetophenone, dimethoxyacetophenone, diethoxyacetophenone, 2-hydroxy-2-methyl-1-phenylpropan-1-one, 2-benzyl-2-dimethylamino-1-(4-morpholinophenyl)-butan-1-one, 2-methyl-1-[4(methoxythio)-phenyl]-2-morpholinopropan-2-one, diphenylacylphenyl phosphinoxide, diphenyl(2,4,6-trimethylbenzoyl) phosphinoxide, 2,4,6-trimethylbenzoylethoxyphenyl phosphinoxide, 2-isopropylthioxantone, 4-isopropylthioxanthone, 2,4-dimethylthioxanthone and their oligomeric counterparts.

The substrate to be printed upon may be composed of any typical substrate material such as paper, plastics, metals, and composites. The substrate may be print stock typically used for publications or may be a packaging material in the form of a sheet, a container such as a bottle or can, or the like. In most instances, the packaging material is a polyolefin such as a polyethylene or a polypropylene, a polyester such as polyethylene terephthalate, or a metal such as an aluminum foil, a metalized polyester, or a metal container.

The radiation curable compositions of the present invention are especially suitable for such applications in which no small molecules which have the tendency to migrate or are suspected to cause health risks, are present. Such applications are, for example, the coating of (food) packaging articles where especially small photoinitiator molecules are undesirable.

Once the energy curable composition is applied to the packaging material, it may be used to contain any kind of liquid or solid material such as foods, drinks, cosmetics, biological materials or specimens, pharmaceuticals, etc.

EXAMPLES

The following examples illustrate specific aspects of the present invention and are not intended to limit the scope thereof in any respect and should not be so construed.

Molecular Weight Determination:

Molecular weight was measured by Gel Permeation Chromatography (GPC) using three GPC columns (manufactured by PSS (Polymer Standards Service-USA, Inc.), SDV 5 µm 1000 Å, SDV 5 µm 500 Å, SDV 5 µm 100 Å, at a flow rate of 1.0 ml/min, eluted with tetrahydrofuran (THF), and at a column temperature of 40° C., mono-disperse polystyrene equivalent molecular weight calibration. A differential refractive index detector (RI) and a UV-detector (254 nm) were used. The dispersibility (Mw/Mn) was calculated from the measurement results.

UV-Spectra Measurement:

Spectra were acquired using a Unicam UV-2 UV/VIS spectrophotometer. All absorption spectra were obtained using 1 cm cuvettes, scanning within the 200-800 nm range. Solutions were prepared in a 100 ml volumetric flask, and, if required, subsequently diluted so that a maximum absorbance of less than 2 was obtained. From the absorption the molar extinction coefficient was calculated in liter·$mol^{-1}·cm^{-1}$.

Method of Determining Set-Off:

Set-off is defined as the tendency of ink to transfer from a freshly printed surface to another paper when pressed without any friction. Set-off is an unwanted behavior of paper and ink. It is influenced by the characteristics of the paper and ink: a porous paper surface absorbs the ink fast results in lesser set-off as do inks that dry (or set) quickly. The higher the speed of the press, the higher the set-off will be.

Set-off is measured at a specific time interval: 1 s. A freshly printed surface is pressed against a paper after 1 s. Then the set-off density is measured.

UV cured prints of inks, which were printed with a comparable density of 1.5 to 1.55, were covered with a white counter paper. Then, with a pressure of 10 tons, both the printed substrate and the plain counter paper were pressed together. Then, the counter paper was removed from the print and the amount of transferred ink on the counter paper was measured by a densitometer. The optical density (OD) of the transferred ink was measured. A lower the amount of transferred ink provides lower readings on the densitometer, which represent better cure.

Example for a Precursor of Formula I

CAS 52830-65-6 is registered in TSCA, DSL and Reach (List of pre-registered substances). The compound is commercially available from a number of suppliers.

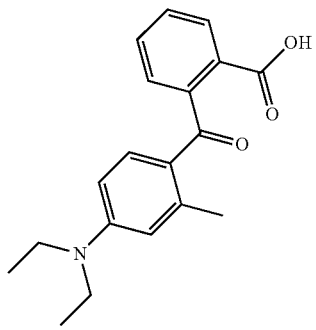 [SMILES: CCN(CC)c1ccc(C(=O)c2ccccc2C(=O)O)c(C)c1]

Inventive Example 1: Synthesis of an Aminoketone of the General Formula I

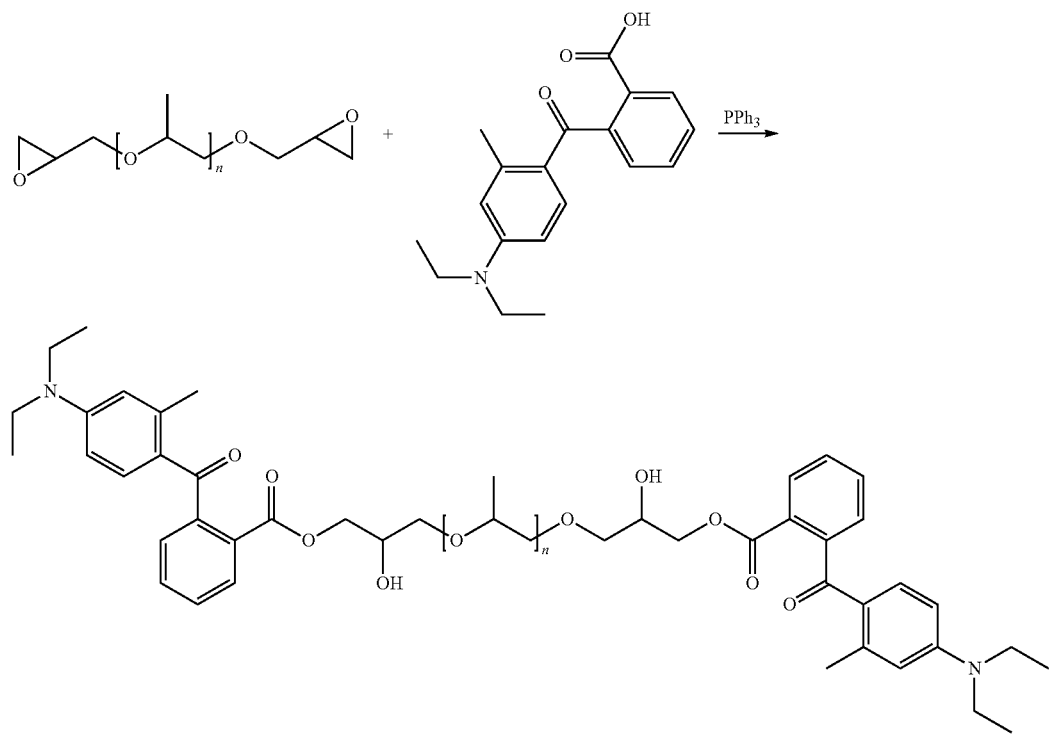

62.2 g (0.2 mol) of 2-[4-(diethylamino)-2-methylbenzoyl] benzoic acid (commercially available e.g. from Chemos CAS 52830-65-6) was mixed with 70.4 g (0.11 mol) of polypropylene glycol di-glycidylether (Sigma Aldrich, Mn: 640 g/mol) and 250 mg of triphenylphosphine. Then, the reaction mixture was stirred and heated under a Nitrogen stream to 100-115° C. for one hour. An amber colored clear liquid is obtained. GPC confirms the full conversion of the starting materials.

Characterization:
GPC: Mn/Mw: 1140/2500 Da
Absorption maximum: 338 nm
Molar extinction coefficient: 48,900 [liter·mol$^{-1}$·cm$^{-1}$]

Evaluation of Inventive Example 1 in Offset Inks Against a STD PI Blend Using a Thioxanthone The performance of Inventive Example 1 was assessed in a magenta offset ink formulation. The inks were printed onto a carton board substrate (Incada Exel coated board from Iggesund) to a density of approximately 1.5 to 1.6 for magenta using an IGT C1 print proofer. These were cured using a Fusion UV rig fitted with a single medium pressure mercury bulb. Prints of each of the inks were cured up to four times/passes with a UV-dose of 33 mJ/cm$^2$ per pass. Table 2 gives a measure for the cure by a "Set-off cure test" which is done by visually comparing the extent to which after each pass the ink has transferred to a piece of blank substrate under 10 tons pressure as described in the protocol for the set-off test.

The photoinitiator (PI) blends used for the evaluation are shown in Table 1 below:

Example 2 (Comparative with Thioxanthone Based PI) & Example 3 (Inventive with Compound Prepared as Described in Example 1)

TABLE 1

Photoinitiator blends for Offset Magenta Ink

|  | Example 2 PI-Blend (Comparative) | Example 3 PI-Blend (Inventive) |
|---|---|---|
| Omnipol TX | 25 |  |
| Compound as obtained in Example 1 |  | 25 |
| Genopol AB-2 | 20 | 20 |
| Omnipol BP | 45 | 45 |
| Irgacure 369 | 10 | 10 |

TABLE 2

Offset Magenta Inks containing the PI-blends given in Table 1:

|  | Ex. 4 ELM[1] Ink (Comparative) | Ex. 5 ELM Ink (Inventive) | Ex. 6 ULR[2] Ink (Comparative) | Ex. 7 ULR Ink (Inventive) |
|---|---|---|---|---|
| Magenta ELM27 | 85 | 85 |  |  |
| Magenta ULR27 without PI-blend |  |  | 85 | 85 |
| Ex. 2 PI Blend Comparative | 15 |  | 15 |  |
| Ex. 3 PI Blend Inventive |  | 15 |  | 15 |
| Total | 100 | 100 | 100 | 100 |
| Viscosity @50/s | 33.2 | 31.8 | 38.6 | 40.2 |
| Viscosity @100/s | 30.1 | 29.3 | 31.6 | 32.6 |

TABLE 2-continued

Offset Magenta Inks containing the PI-blends given in Table 1:

|  | Ex. 4 ELM[1] Ink (Comparative) | Ex. 5 ELM Ink (Inventive) | Ex. 6 ULR[2] Ink (Comparative) | Ex. 7 ULR Ink (Inventive) |
|---|---|---|---|---|
| Cure Rating – Set-off test STD-UV (OD of print) | 1.6 | 1.5 | 1.45 | 1.5 |
| Pass 1 33 mJ/cm$^2$ | 0.30 | 0.25 | 0.30 | 0.15 |
| Pass 2 66 mJ/cm$^2$ | 0.10 | 0.06 | 0.00 | 0.02 |
| Pass 3 99 mJ/cm$^2$ | 0.00 | 0.00 | 0.00 | 0.00 |
| Cure Rating – Set-off test H-UV | 1.5 | 1.5 | 1.5 | 1.5 |
| Pass 1 33 mJ/cm$^2$ | 0.18 | 0.45 | 0.12 | 0.25 |
| Pass 2 66 mJ/cm$^2$ | 0.03 | 0.19 | 0.03 | 0.09 |
| Pass 3 99 mJ/cm$^2$ | 0.01 | 0.08 | 0.02 | 0.03 |
| Pass 4 132 mJ/cm$^2$ | 0.01 | 0.05 | 0.02 | 0.02 |

[1]ELM is a commercially available EB-offset-ink from SunChemical Corporation. An EB-ink doesn't contain a PI-blend and is intended for cure with an electron-beam. However, by the addition of the PI-blend the EB-ink becomes a UV-curable offset ink.
[2]ULR is a commercially available UV-offset-ink from SunChemical Corporation. The magenta UV-offset ink was used as a base containing no PI-blend. In order to directly compare the inventive PI against the STD thioxanthone based PI-blend, these PI-blends were mixed into the magenta base inks.

The data of the set-off test provided in Table 2 shows that the reactivity of the inventive PI-blend is comparable to the thioxanthone based PI-blend used in the STD. The data shows that it is possible to make a UV-curable low migration ink without using a thioxanthone derivative.

The present invention has now been described in detail, including the preferred embodiments thereof. However, it will be appreciated that those skilled in the art, upon consideration of the present disclosure, may make modifications and/or improvements on this invention that fall within the scope and spirit of the invention.

What is claimed is:

1. An aminoketone of the general Formula I:

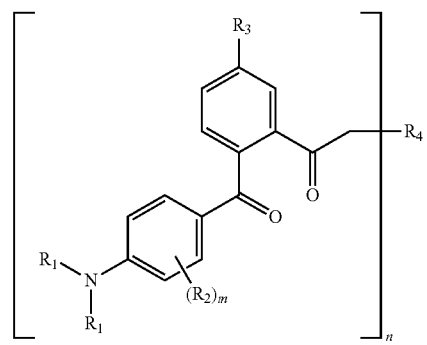

wherein
each $R^1$ is independently selected from branched or unbranched $C_{1-12}$ alkyl, or $C_{3-12}$ cycloalkyl radical; each of which is independently optionally substituted with $R^5$;

$R^4$ is selected from the group consisting of a di-, tri-, tetra-, penta- and hexavalent alkyl radical, wherein $CH_2$ groups may optionally be replaced by an oxygen or substituted by hydroxyl-functions as a result of the reaction with glycidyl or epoxy-compounds;

$R^3$ is selected from the group consisting of H, a branched or unbranched $C_{1-12}$ alkyl, and a $C_{3-12}$ aryl radical;

each $R^5$ is independently selected from the group consisting of oxygen, nitrogen, and sulfur;

each $R^2$ is independently selected from branched or unbranched $C_{1-12}$ alkyl, or $C_{3-12}$ cycloalkyl, preferably $C_1$ to $C_4$ alkyl, $R^2$ can substitute one (m=1), two (m=2), three (m=3), or all four (m=4) hydrogens on the aromatic ring bearing the amino-substituent; and when $R^4$ is formed by the reaction with a glycidyl ether or epoxy-compounds then n denotes an integer from 1 to 4; in all other instances, n denotes an integer from 2 to 6.

2. A UV-curable composition comprising one or more aminoketones of claim 1 and one or more acrylates.

3. The composition of claim 2, which is a UV-curable coating or ink.

4. The UV-curable coating or ink of claim 3 that is curable with UV light having a wavelength of 310-400 nm.

5. The UV-curable coating or ink of claim 3, further comprising a colorant.

6. A UV-curable coating or ink comprising an aminoketone according to claim 1, wherein the coating or ink is capable of being cured by a light emitting diode (LED).

7. The UV-curable coating or ink according to claim 2, comprising no splitting type photoinitiators.

8. A low migration printed material comprising the coating or ink of claim 2.

9. A cured material, obtained by curing the UV-curable coating or ink of claim 2 with UV radiation.

* * * * *